(12) United States Patent
Hognon et al.

(10) Patent No.: US 10,463,987 B2
(45) Date of Patent: Nov. 5, 2019

(54) PROCESS FOR PURIFYING AN AQUEOUS SOLUTION COMPRISING DIETHYLACETAL

(71) Applicants: IFP Energies Nouvelles, Rueil-Malmaison (FR); Compagnie Generale des Etablissements Michelin, Clermont-Ferrand (FR)

(72) Inventors: Celine Hognon, Mions (FR); Sophie Drozdz, Brindas (FR); Marc Jacquin, Lyons (FR); Damien Leinekugel Le Cocq, Oullins (FR); Frederic Augier, Saint Symphorien d'Ozon (FR)

(73) Assignees: IFP Energies Nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/342,269

(22) PCT Filed: Oct. 13, 2017

(86) PCT No.: PCT/EP2017/076229
§ 371 (c)(1),
(2) Date: Apr. 16, 2019

(87) PCT Pub. No.: WO2018/073129
PCT Pub. Date: Apr. 26, 2018

(65) Prior Publication Data
US 2019/0232193 A1  Aug. 1, 2019

(30) Foreign Application Priority Data
Oct. 17, 2016  (FR) .................................... 16 60015

(51) Int. Cl.
| C07C 29/00 | (2006.01) |
| C07C 45/80 | (2006.01) |
| B01D 11/00 | (2006.01) |
| B01D 11/04 | (2006.01) |
| C07C 29/88 | (2006.01) |

(52) U.S. Cl.
CPC ...... *B01D 11/0426* (2013.01); *B01D 11/0488* (2013.01); *B01D 11/0492* (2013.01); *C07C 29/88* (2013.01); *C07C 45/80* (2013.01); *B01D 2011/002* (2013.01)

(58) Field of Classification Search
CPC ...... C07C 29/88; C07C 45/80; B01D 11/0426
See application file for complete search history.

(56) References Cited

U.S. PATENT DOCUMENTS

| 9,950,969 B2 | 4/2018 | Dastillung et al. |
| 2017/0267604 A1 | 9/2017 | Dastillung et al. |
| 2017/0291859 A1 | 10/2017 | Dastillung et al. |

FOREIGN PATENT DOCUMENTS

| FR | 3026100 A1 | 3/2016 |
| FR | 3026101 A1 | 3/2016 |

OTHER PUBLICATIONS

International Search Report dated Jan. 29, 2018 issued in corresponding PCT/EP2017/076229 application (2 pages).

*Primary Examiner* — Sikarl A Witherspoon
(74) *Attorney, Agent, or Firm* — Millen, White, Zelano and Branigan, P.C.

(57) ABSTRACT

The invention relates to a process for purifying an aqueous solution comprising ethanol, acetaldehyde and diethylacetal comprising: a step A) of countercurrent liquid-liquid extraction comprising an extraction section supplied at the top by said aqueous solution as a mixture with at least one fraction of the water/ethanol/acetaldehyde raffinate resulting from the back extraction step B), and at the bottom by an extraction solvent, and producing an extract at the top and a purified feedstock at the bottom; —a step B) of countercurrent liquid-liquid back extraction comprising a back extraction section supplied at the top by an acidic aqueous solution, the pH of which is between 0.5 and 5, and at the bottom by the extract resulting from step A), and producing an extract at the top and a water/ethanol/acetaldehyde raffinate at the bottom.

10 Claims, 1 Drawing Sheet

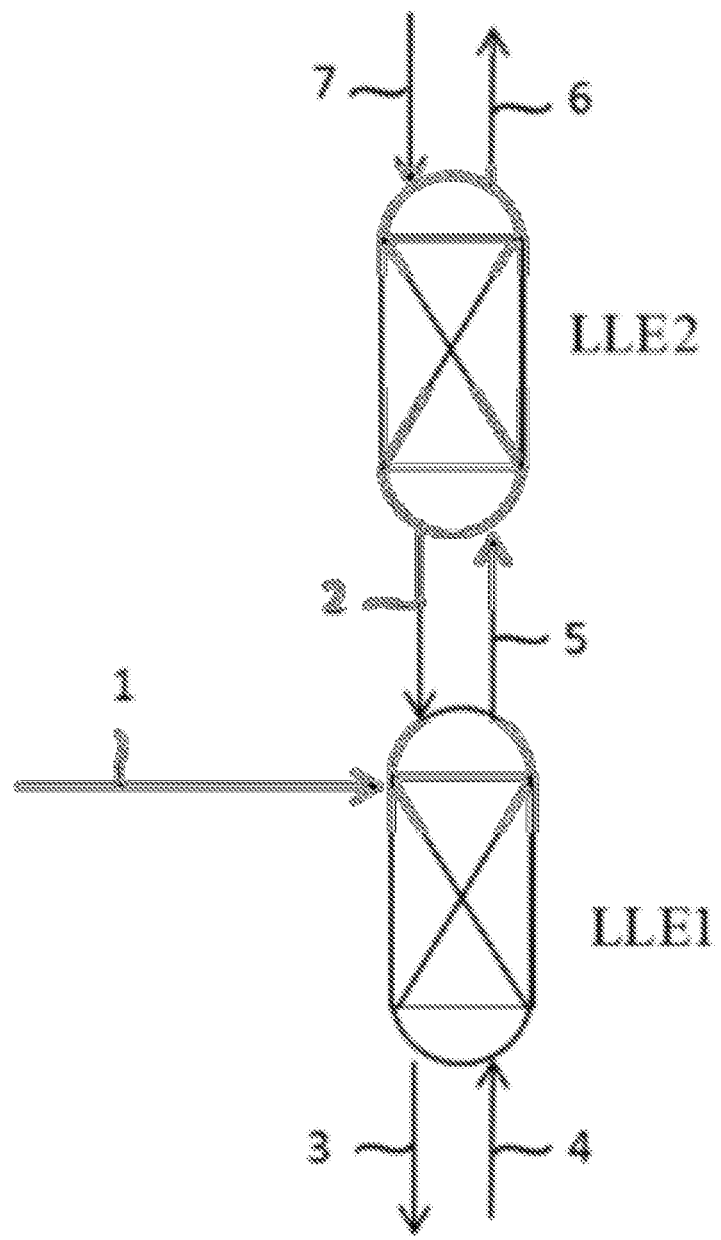

PROCESS FOR PURIFYING AN AQUEOUS SOLUTION COMPRISING DIETHYLACETAL

TECHNICAL FIELD OF THE INVENTION

The present invention relates to the improvement in the recovery of ethanol and acetaldehyde in the liquid effluents from Lebedev reactors.

PRIOR ART

The process for the production of butadiene from ethanol was developed in particular by American teams during the Second World War starting from the studies of Ostromilenski.

In this process, the conversion per pass is a less than 50%, which implies significant recyclings of the ethanol and acetaldehyde. Furthermore, a great variety of impurities of different natures (saturated, unsaturated or aromatic hydrocarbons, oxygen-comprising products such as alcohols, ketones, aldehydes, phenols, acids, esters, ethers) and having very different molar masses is produced (between 50 and 10 000 g/mol).

It is thus necessary to put in place a line of unit operations with the aim of removing as much as possible of impurities while losing as little as possible of ethanol and acetaldehyde. From an economic viewpoint, it is essential to reduce the production cost of butadiene, which requires:

losing as little ethanol and acetaldehyde as possible
not recycling impurities in the reactors, which impurities would result in a fall in selectivity for butadiene or would accumulate at unacceptable levels, requiring a purge and thus losses of ethanol and acetaldehyde.

At the outlet of the catalytic reactors, the effluent produced, composed of butadiene, acetaldehyde, water, ethanol and impurities, undergoes several unit operations in order to separate the gaseous byproducts from the liquid byproducts, liquid and gaseous being understood at ambient temperature and pressure.

Mention may be made, among the gaseous byproducts, of hydrogen, carbon monoxide, carbon dioxide, $C_1$-$C_4$ olefins and alkanes. It is essential to remove these byproducts from the butadiene-rich effluent in order to obtain a product within specifications.

Mention may be made, among the byproducts which are liquid at ambient temperature, of acetone, diethyl ether, butanal, butanol, butanone, ethyl acetate, crotonaldehyde and acetic acid. Other byproducts are generated in a smaller amount in the reaction zone. In the continuation of the document, "impurities" will denote this combination of thousands of hydrocarbon or oxygen-comprising compounds.

In the first process schemes of the American teams, ethanol, acetaldehyde, water and the liquid byproducts were separated by a line of three distillation columns (U.S. Pat. No. 2,403,742). The effluent rich in ethanol, acetaldehyde, water and liquid byproducts feeds a first distillation column in which an acetaldehyde-rich effluent is separated from the remainder of the effluent. A second distillation column makes it possible to separate the liquid byproducts from an effluent rich in ethanol and water. The final distillation column makes it possible to separate the ethanol from the water. Most of the process patents filed in the period 1940-1960 by Carbide & Carbon or Koppers (U.S. Pat. Nos. 2,403,743, 2,393,381, 2,395,057 and 2,439,587) are targeted at improving this part of the scheme.

One of the problems of the process, observed in the 1945s, is a significant formation of diethyl acetal, resulting in a not insignificant loss of reactants and thus of yield of butadiene. Toussaint et al., Industrial and Engineering Chemistry, 1947, Vol. 39, No. 2, pp. 120-125, indicate that 20 kg of diethyl acetal are produced per tonne of butadiene formed.

In the patents FR 3 026 100 and FR 3 026 101, the liquid impurities are removed by liquid-liquid extraction. The effluent composed of ethanol, acetaldehyde, water and impurities feeds a liquid-liquid extraction column. The latter is fed at the bottom with a scrubbing solvent, the aim of which is to scrub the feedstock countercurrentwise. At the outlet of this scrubbing section, the extract is predominantly composed of the scrubbing solvent, of the extracted byproducts and of a small amount of ethanol and acetaldehyde. This extract is subsequently scrubbed with water with the aim of re-extracting the ethanol and the acetaldehyde and thus minimizing the losses of ethanol and acetaldehyde. The scrubbing solvent employed for this unit operation consists of a mixture of hydrocarbons having between 6 and 40 carbon atoms.

In this configuration, a high proportion of the diethyl acetal and approximately half of the corresponding hemiacetal, formed upstream of the liquid-liquid extraction stage, are extracted by the solvent. This has the consequence of resulting in a not insignificant loss of ethanol and acetaldehyde equivalent and thus of increasing the production cost of the butadiene. An object of the invention is to improve the recovery of the ethanol and of the acetaldehyde and advantageously applies to the ethanol/acetaldehyde/water effluent resulting from D1) of FR 3 026 100, or the ethanol/acetaldehyde/water effluent resulting from stage B) of FR 3 026 101.

Object and Advantage of the Invention

The invention relates to a sequence of unitary operations for the extraction of the impurities and the decomposition of the diethyl acetal present in a feedstock of Lebedev type composed of water, ethanol, acetaldehyde and impurities.

The applicant has discovered that, by controlling a certain number of operating parameters, such as the pH of the aqueous solution used to carry out the re-extraction stage and the temperature of the liquid-liquid extraction, it was possible, surprisingly, to limit the losses of ethanol and acetaldehyde during the extraction of the diethyl acetal and of the hemiacetal. The use of acidified water to carry out the back-extraction of the ethanol and of the acetaldehyde, the increase of the temperature and of the residence time in the extractor can, under specific conditions, improve the performances of the process for the production of butadiene from ethanol.

DETAILED DESCRIPTION OF THE INVENTION

The invention relates to a process for the purification of an aqueous solution comprising at least ethanol, acetaldehyde and diethyl acetal, comprising a stage A) of countercurrentwise liquid-liquid extraction comprising an extraction section fed at the top with said aqueous solution mixed with at least a fraction of the water/ethanol/acetaldehyde raffinate resulting from the re-extraction stage B), this mixture constituting the feedstock of said extraction section of said stage A), and at the bottom with an extraction solvent, and producing, at the top, an extract and, at the bottom, a purified feedstock, carried out at a temperature of between 10 et 40° C. and at a pressure of between 0.1 and 0.5 MPa with a flow rate by weight of continuous phase/flow rate by weight of dispersed phase ratio of less than 70;

a stage B) of countercurrentwise liquid-liquid re-extraction fed at the top with an aqueous acidic solution, the pH of which is between 0.5 and 5, and at the bottom with the extract resulting from stage A), and producing, at the top, an extract and, at the bottom, a water/ethanol/acetaldehyde raffinate, carried out at a temperature of between 10 and 90° C. and at a pressure of between 0.1 and 0.5 MPa with a flow rate by weight of continuous phase/flow rate by weight of dispersed phase ratio of less than 70, preferably of less than 35, in a preferred way of less than 10, and preferably of less than 3.

Feedstock of the Process

The process according to the invention makes it possible to extract the ethanol and the acetaldehyde from an aqueous solution comprising ethanol, acetaldehyde, diethyl acetal and impurities. The impurities can be of highly varied natures (saturated, unsaturated or aromatic hydrocarbons, oxygen-comprising products, among which may be mentioned alcohols, ketones, aldehydes, phenolic compounds, acids, esters, ethers), it being possible for the molar masses of the different impurities to range from 50 to 10 000 g/mol. Mention may be made, among the typical impurities, of acetone, diethyl ether, butanal, butanols, butanones, ethyl acetate, crotonaldehyde, pentenes, pentadienes, hexenes and hexadienes.

Said purification process is fed with an aqueous solution comprising at least ethanol, acetaldehyde and diethyl acetal.

Preferably, the content of ethanol in said aqueous solution is between 40% and 70 weight %, preferably between 50 and 60 weight %, the content of acetaldehyde is between 1 et 30 weight %, preferably between 5 and 10 weight %, and the content of impurities is between 1 and 20 weight %, preferably between 5 and 20 weight %. The content of diethyl acetal in said aqueous solution is preferably between 1 and 20 weight % and preferably between 1 and 15 weight %. Said aqueous solution is advantageously an effluent from conversion of ethanol, or of an ethanol/acetaldehyde mixture, into 1,3-butadiene, after separation of the non-condensables and of the butadiene. This aqueous solution is preferably an effluent similar to the ethanol/acetaldehyde/water effluent resulting from D1) of FR 3 026 100, or the ethanol/acetaldehyde/water effluent resulting from stage B) of FR 3 026 101, or any other equivalent process effluent of Lebedev type.

Stage A) of Extraction of the Impurities

The purification process according to the invention comprises a stage A) of countercurrentwise liquid-liquid extraction comprising an extraction section fed at the top with said aqueous solution mixed with the raffinate resulting from the re-extraction stage B), this mixture constituting the feedstock of said extraction section, and at the bottom with an extraction solvent, and producing, at the top, an extract and, at the bottom, a purified feedstock, carried out at a temperature of between 10 et 70° C. and at a pressure of between 0.1 and 0.5 MPa, preferably between 0.2 and 0.4 MPa, with a flow rate by weight of continuous phase/flow rate by weight of dispersed phase ratio of less than 70, preferably of less than 35, in a preferred way of less than 10, and preferably of less than 3, preferably of less than 1.5. Above 70, the hydrodynamic operation of the extraction section is compromised. It does not matter whether the extraction solvent forms the continuous or dispersed phase, this criterion being a hydrodynamic criterion.

The residence time in the extraction section of said stage A) is adjusted so as to obtain the performance qualities desired in terms of degree of recovery, as is known to a person skilled in the art. It is typically between 0.5 and 10 h, advantageously between 0.5 and 6 h.

As known to a person skilled in the art, a liquid-liquid extraction operates with two liquid phases, one of the phases constituting the continuous phase and the other constituting the dispersed phase, present in the form of distinct drops. The continuous or dispersed nature depends on the relative flow rate of one phase with respect to the other. Thus, according to the well-known phenomenon, if the flow rate of the continuous phase is reduced while increasing the flow rate of the dispersed phase, the dispersed phase will become continuous, and vice versa.

Said extract produced at the top of said extraction section of said stage A) preferably comprises more than 80 weight % of the impurities, between 20 and 50 weight % of the ethanol and of the acetaldehyde and more than 90% of the diethyl acetal which are present in said feedstock of said extraction section of said stage A).

Said purified feedstock produced at the bottom of said extraction section of said stage A) comprises water and between 80 and 100 weight % of the ethanol and of the acetaldehyde which are present in said aqueous solution feeding the process according to the invention. In other words, between 80% and 100% of the ethanol and of the acetaldehyde feeding the process according to the invention are recovered in said purified feedstock.

The extraction solvent and the aqueous solution feeding said stage A) are each fed at a temperature independently of between 10 and 70° C., preferably between 20 and 55° C.

The greater the ratio of the flow rate by weight of extraction solvent to the flow rate by weight of the feed of said extraction section of said stage A), the more effective the stage of extraction of the impurities. However, a high ratio results in a significant fraction of ethanol and of acetaldehyde also being extracted in the extract of said stage A) and consequently in the flow rate of aqueous acidic solution necessary within stage B) being increased in order to limit the losses of ethanol and acetaldehyde. The value of the ratio of flow rate by weight of extraction solvent to the flow rate by weight of aqueous acidic solution thus has to be adjusted so as to extract the maximum of impurities while limiting the losses of ethanol and acetaldehyde.

The ratio of flow rate by weight of extraction solvent to the flow rate by weight of aqueous acidic solution is adjusted so that said extract resulting from stage B) comprises 50 weight %, preferably 60 weight % and in a preferred way 70 weight % of the impurities present in said aqueous solution feeding said stage A), and also at most 5 weight %, preferably at most 2 weight % and in a preferred way at most 1 weight % of the total amount of ethanol and of acetaldehyde present in said aqueous solution feeding said stage A).

Said extraction solvent which feeds stage A) is advantageously a mixture of hydrocarbons having between 6 and 40 carbon atoms, preferably between 10 and 20 carbon atoms, or any other solvents which make possible a phase separation with the aqueous/alcoholic phase. In a nonlimiting way, said mixture of hydrocarbons can be a desulfurized gas oil or kerosene cut or alternatively a hydrocarbon cut produced by a unit of Fischer-Tropsch type.

This stage is configured so as to extract the maximum of impurities and the minimum of ethanol and acetaldehyde. In such a configuration, as the diethyl acetal is much less polar than the ethanol and the acetaldehyde, it is extracted quantitatively with the impurities.

An important point to note is that, within said feedstock feeding stage A), the concentration of diethyl acetal is lower than the thermodynamic equilibrium of the reaction for the conversion of the ethanol and the acetaldehyde into diethyl acetal. This is because said feedstock originates from a catalytic reactor operating at high temperature (temperature where the diethyl acetal is quantitatively decomposed) and is then subjected to a certain number of unit separation operations at a moderate temperature (favorable to the formation of diethyl acetal) but a priori with a residence time too low for the amount of diethyl acetal formed to reach thermodynamic equilibrium.

The contact between the two liquid phases in said extraction section is carried out within a liquid-liquid contactor. Various contact forms can be envisaged. Mention may be made, in a nonlimiting way, of a packed column, a pulsed column, an agitated partitioned column or else a mixer-settler battery. Said extract of said stage A) feeds stage B) of re-extraction of the ethanol and of the acetaldehyde.

Stage B) of Re-Extraction of the Ethanol and of the Acetaldehyde

The purification process according to the invention comprises a stage B) of countercurrentwise liquid-liquid re-extraction comprising a re-extraction section fed at the top with an aqueous acidic solution having a pH of between 0.5 and 5, and at the bottom with the extract resulting from stage A), and producing, at the top, an extract and, at the bottom, a water/ethanol/acetaldehyde raffinate, carried out at a temperature of between 10 and 70° C., preferably between 20 and 55° C., and at a pressure of between 0.1 and 0.5 MPa, preferably between 0.2 and 0.4 MPa, a residence time of between 0.5 and 6 h, advantageously between 1 and 3 h, with a flow rate by weight of continuous phase/flow rate by weight of dispersed phase ratio of less than 70, preferably of less than 35, in a preferred way of less than 10, and preferably of less than 3, preferably of less than 1.5, the hydrodynamic operation of the re-extraction section being compromised above 70.

The residence time is defined as the mean time necessary for a water molecule injected with the aqueous acidic solution feeding said re-extraction section of said stage B) to be extracted in the water/ethanol/acetaldehyde raffinate resulting from said re-extraction section of said stage B). This residence time is conventionally determined by measurement of RTD or Residence Time Distribution, in which a marker (colorant or other) is injected from time to time at the inlet, the concentration of this marker being observed at the outlet.

Said aqueous acidic solution which feeds stage B) is acidified water, that is to say a water having a pH of between 0.5 and 5, preferably between 2 and 4 and in a preferred way between 2.5 and 3.5, and advantageously contains less than 2 weight % of the ethanol+acetaldehyde total, that is to say that the sum of the contents by weight of ethanol and acetaldehyde is less than 2 weight % of said aqueous solution, preferably less than 1 weight %, and very preferably not containing either ethanol or acetaldehyde. The water can nonlimitingly contain strong acids and/or weak acids. Nonlimitingly, it is possible to employ, in order to acidify the water, a weak acid, such as acetic acid, or a strong acid, such as sulfuric acid or nitric acid.

The applicant has observed that particularly advantageous performance qualities were obtained if the residence time tin said re-extraction section of said re-extraction stage B), expressed in hours, and the pH of the aqueous acidic solution feeding said stage B) were adjusted jointly so that $pH-\log_{10}(t/t_0)$ is between 1 and 4, preferably between 1.5 and 3 and advantageously between 1.8 and 2.5, $t_0$ representing a reference time equal to 1 h. $\log_{10}(x)$ is understood to mean the logarithm in base 10 of x, equal to $\ln(x)/\ln(10)$.

Said aqueous acidic solution and said extract resulting from stage A) are fed independently at a temperature of between 10 and 70° C., preferably between 20 and 55° C.

The extract resulting from stage B) can be treated in a separation stage in order to recover and to recycle the extraction solvent to the extraction stage A).

At least a fraction of the raffinate produced at the bottom of said re-extraction section of said stage B), advantageously all of said raffinate, is mixed with the aqueous solution feeding said stage A). Even when all of said raffinate is recycled and as is common practice in the case of recycling, a withdrawal can be carried out, continuously or noncontinuously, on said raffinate, known as purge, in order to limit the accumulation of the impurities in this raffinate.

The contact between the two liquid phases in said re-extraction section of said re-extraction stage B) is advantageously carried out within a liquid-liquid contactor. Various contact forms can be envisaged.

Mention may be made, in a nonlimiting way, of a packed column, a pulsed column, an agitated partitioned column or else a mixer-settler battery.

For a person skilled in the art, the higher the temperature, the lower the pH and the greater the residence time within the unit separation operations, the more diethyl acetal should be formed, as this results in the reaction kinetics being increased while allowing the reaction more time to take place, which results in an increase in the losses of ethanol and acetaldehyde and increases the content of diethyl acetal in the extract. In point of fact, the process according to the invention employs a low pH in the re-extraction stage and a relatively high residence time, while resulting in a better recovery of the ethanol and of the acetaldehyde.

Surprisingly, the applicant has discovered that, by controlling a certain number of operating parameters, such as the pH of the acidified water or the temperature of the section for re-extraction of the ethanol and of the acetaldehyde, and/or by modifying the form of contacting (residence time and technology), it was possible, surprisingly, to limit the losses of ethanol and acetaldehyde.

Advantageously, stage B) will be carried out so that the aqueous phase constitutes the continuous phase of said re-extraction section of said stage B), while stage A) will be carried out so that the organic phase constitutes the continuous phase of said extraction section of said stage A).

DESCRIPTION OF THE FIGURES

FIG. 1 represents, diagrammatically and nonlimitingly, an arrangement of the process according to the invention.

The aqueous solution comprising ethanol, acetaldehyde and diethyl acetal (1) feeds, at the top, a liquid-liquid extraction column LLE1 in which stage A) is carried out. The latter is fed, at the top, with a water/ethanol/acetaldehyde raffinate (2) resulting from the liquid-liquid extraction column LLE2 in which stage B) is carried out and, at the bottom, with the extraction solvent (4). The extract (5) is withdrawn at the top of the column while a purified feedstock (3) is withdrawn at the bottom of the column.

The extract (5) feeds, at the bottom, the second liquid-liquid extraction column LLE2, which is also fed, at the top, with an aqueous acidic solution (7). The extract (6) is withdrawn at the top while, at the bottom of the column, a water/ethanol/acetaldehyde raffinate (2) is withdrawn and feeds the first liquid-liquid extraction column LLE1.

EXAMPLES

In all the examples which follow, an aqueous solution comprising ethanol, acetaldehyde and water exhibiting the following composition is treated:
48 weight % of ethanol
9 weight % of acetaldehyde
42 weight % of water
1 weight % of diethyl ether Example 1 (not in Accordance)

In this example, the re-extraction stage is carried out with pure water.
Liquid-Liquid Extraction Stage A)
The aqueous solution comprising ethanol, acetaldehyde and water is injected at the top of the stirred pilot-scale liquid-liquid extraction column of Kuhni (ECR) type with a working height of 1.8 m and with an internal diameter of 32 mm, provided with a stirrer shaft with stirring rotors and 40% perforation plates. Hexadecane is injected at the bottom as extraction solvent. The operating conditions are as follows:
Temperature: 23° C.
Continuous organic phase, dispersed aqueous phase
Feedstock flow rate: 4.8 l/h
Solvent flow rate: 5.2 l/h
Stirring speed: 200 rotations per minute
Re-Extraction Stage B)
The extract withdrawn at the top of the extraction column is fed at the bottom of a re-extraction column. The re-extraction column is identical to the extraction column (stage A). This column is fed at the top with pure water, the aqueous phase constituting the dispersed phase. The raffinate withdrawn at the column bottom is mixed with the aqueous solution feeding stage A).
The following performances are obtained:
The ethanol yield, defined as the flow rate of recovered ethanol in the purified feedstock withdrawn at the bottom of the column of stage A) relatively to the flow rate of ethanol in the aqueous solution feeding stage A), is 96%.
The acetaldehyde yield, defined as the flow rate of recovered acetaldehyde in the purified feedstock withdrawn at the bottom of the column of stage A) relatively to the flow rate of acetaldehyde in the aqueous solution feeding stage A), is 91%.

Example 2 (in Accordance)

In this example, the re-extraction stage B) is carried out with an aqueous acidic solution, the organic phase constituting the continuous phase of stage B).
The extraction stage A) is carried out identically to Example 1.
The extract withdrawn at the top of the extraction column is fed at the bottom of a re-extraction column. The re-extraction column is identical to the extraction column (stage A). This column is fed at the top with an aqueous solution containing 3 weight % of acetic acid (i.e., a pH of approximately 2.5), the aqueous phase constituting the dispersed phase.

On carrying out the re-extraction with acidified water as dispersed phase, the following performances are obtained:
The ethanol yield, defined as the flow rate of recovered ethanol in the purified feedstock withdrawn at the bottom of the column of stage A) relatively to the flow rate of ethanol in the aqueous solution feeding stage A), is 97%.
The acetaldehyde yield, defined as the flow rate of recovered acetaldehyde in the purified feedstock withdrawn at the bottom of the column of stage A) relatively to the flow rate of acetaldehyde in the aqueous solution feeding stage A), is 92.5%.
The performances are improved with respect to the prior art in which pure water is used as re-extraction solvent.

Example 3 (in Accordance)

In this example, the re-extraction stage B) is carried out with an aqueous acidic solution, the aqueous phase constituting the continuous phase of stage B).
The extraction stage A) is carried out identically to Examples 1 and 2.
The extract withdrawn at the top of the extraction column is fed at the bottom of a re-extraction column. The re-extraction column is identical to the extraction column (stage A). This column is fed at the top with an aqueous solution containing 3 weight % of acetic acid (i.e., a pH of approximately 2.5), the aqueous phase constituting the dispersed phase.
On carrying out the re-extraction with acidified water as continuous phase, the following performances are obtained:
The ethanol yield, defined as the flow rate of recovered ethanol in the purified feedstock withdrawn at the bottom of the column of stage A) relatively to the flow rate of ethanol in the aqueous solution feeding stage A), is greater than 99.5%.
The acetaldehyde yield, defined as the flow rate of recovered acetaldehyde in the purified feedstock withdrawn at the bottom of the column of stage A) relatively to the flow rate of acetaldehyde in the aqueous solution feeding stage A), is 99.2%.
The performances are improved with respect to a continuous organic phase in stage A)/continuous organic phase in stage B) implementation.

The invention claimed is:

1. A process for the purification of an aqueous solution comprising at least ethanol, acetaldehyde and diethyl acetal, comprising
a stage A) of countercurrentwise liquid-liquid extraction comprising an extraction section fed at the top with said aqueous solution mixed with at least a fraction of the water/ethanol/acetaldehyde raffinate resulting from the re-extraction stage B), this mixture constituting the feedstock of said extraction section of said stage A), and at the bottom with an extraction solvent, and producing, at the top, an extract and, at the bottom, a purified feedstock, carried out at a temperature of between 10 et 40° C. and at a pressure of between 0.1 and 0.5 MPa with a flow rate by weight of continuous phase/flow rate by weight of dispersed phase ratio of less than 70;
a stage B) of countercurrentwise liquid-liquid re-extraction comprising a re-extraction section fed at the top with an aqueous acidic solution, the pH of which is between 0.5 and 5, and at the bottom with the extract resulting from stage A), and producing, at the top, an extract and, at the bottom, a water/ethanol/acetaldehyde raffinate, carried out at a temperature of between 10 and 90° C. and at a pressure of between 0.1 and 0.5 MPa, a residence time of between 0.5 and 6 h, with a flow rate by weight of continuous phase/flow rate by weight of dispersed phase ratio of less than 70.

2. The process as claimed in claim 1, in which the content of ethanol in said aqueous solution comprising ethanol, acetaldehyde and diethyl acetal is between 40 and 70 weight %, the content of acetaldehyde is between 1 and 30 weight %, the content of impurities is between 1 and 20 weight % and the content of diethyl acetal is between 1 and 20 weight %.

3. The process as claimed in claim 1, in which said extraction solvent which feeds stage A) is a mixture of hydrocarbons having between 6 and 40 carbon atoms.

4. The process as claimed in claim 1, in which the flow rate by weight of continuous phase/flow rate by weight of dispersed phase ratio in said extraction section of said stage A) is less than 3.

5. The process as claimed in claim 1, in which said aqueous acidic solution which feeds stage B) has a pH of between 2 and 4.

6. The process as claimed in claim 1, in which the residence time t in said re-extraction section of said re-extraction stage B), expressed in hours, and the pH of the aqueous acidic solution feeding said stage B) are adjusted jointly so that $pH-\log_{10}(t/t_0)$ is between 1 and 4, $t_0$ representing a reference time equal to 1 h.

7. The process as claimed in claim 1, in which said aqueous acidic solution which feeds stage B) contains less than 2 weight % of the ethanol+acetaldehyde total.

8. The process as claimed in claim 1, in which said aqueous acidic solution which feeds stage B) contains less than 1 weight % of the ethanol+acetaldehyde total.

9. The process as claimed in claim 1, in which said aqueous acidic solution which feeds stage B) does not contain either ethanol or acetaldehyde.

10. The process as claimed in claim 1, in which the organic phase constitutes the continuous phase of said extraction section of said stage A) and the aqueous phase constitutes the continuous phase of said re-extraction section of said stage B).

* * * * *